United States Patent
Penot et al.

(10) Patent No.: US 10,022,466 B2
(45) Date of Patent: Jul. 17, 2018

(54) SYNCHRONOUS CONTROL OF LAMP BRIGHTNESS AND SAMPLE DIFFUSION

(71) Applicant: Le Labo Inc., New York, NY (US)

(72) Inventors: Fabrice Penot, Brooklyn, NY (US); Kirk Alexander Middlemass, Winchester, CT (US)

(73) Assignee: Le Labo Inc., New York, NY (US)

( * ) Notice: Subject to any disclaimer, the term of this patent is extended or adjusted under 35 U.S.C. 154(b) by 55 days.

(21) Appl. No.: 15/196,888

(22) Filed: Jun. 29, 2016

(65) Prior Publication Data
US 2018/0000978 A1  Jan. 4, 2018

(51) Int. Cl.
*A61L 9/02* (2006.01)
*A61L 9/04* (2006.01)
*H05B 37/02* (2006.01)
*H02P 7/06* (2006.01)

(52) U.S. Cl.
CPC ............ *A61L 9/04* (2013.01); *H02P 7/06* (2013.01); *H05B 37/0209* (2013.01)

(58) Field of Classification Search
CPC ............................ H04L 12/10; H05B 37/0254
See application file for complete search history.

(56) References Cited

U.S. PATENT DOCUMENTS

| | | | | |
|---|---|---|---|---|
| 4,695,434 A * | 9/1987 | Spector | ............... | A01M 1/2077 239/56 |
| 5,115,975 A * | 5/1992 | Shilling | ................. | A61L 9/03 239/136 |
| 5,175,791 A | 12/1992 | Muderlak et al. | | |
| 7,503,675 B2 * | 3/2009 | Demarest | ............ | A01M 1/2072 362/253 |
| 7,572,412 B2 * | 8/2009 | Yang | ..................... | A61L 9/122 392/386 |
| 7,687,744 B2 * | 3/2010 | Walter | ................... | A61L 9/037 219/494 |
| 7,932,482 B2 | 4/2011 | Norwood et al. | | |
| 9,517,286 B1 * | 12/2016 | Li | ........................ | A61L 9/145 |
| 2002/0176704 A1 | 11/2002 | Roe | | |

(Continued)

OTHER PUBLICATIONS

"Sue's Aroma Lamps," http://222.suesaromalamps.com/alamp.php, May 10, 2016, 2 pages.

(Continued)

*Primary Examiner* — Alexander H Taningco
*Assistant Examiner* — Kurtis R Bahr
(74) *Attorney, Agent, or Firm* — Ryan, Mason & Lewis, LLP

(57) ABSTRACT

In response to user interaction, a signal is generated from a control element of a sample diffuser assembly. The sample diffuser assembly comprises a sample container, wherein the sample container is configured to receive a sample to be diffused; a motor operative to assist in diffusing the sample at a selectable transformation rate; a light source, wherein the light source comprises an AC lamp; and control circuitry operatively coupled to the motor and the light source. A set of signals is generated, via the control circuitry in response to the signal generated by the control element, wherein the set of signals simultaneously control the light intensity of the AC lamp based on the transformation rate produced by the motor to diffuse the sample in the sample container.

20 Claims, 7 Drawing Sheets

(56) References Cited

U.S. PATENT DOCUMENTS

| | | | | |
|---|---|---|---|---|
| 2008/0130266 A1* | 6/2008 | DeWitt | ............... | A61L 9/03 |
| | | | | 362/96 |
| 2008/0315777 A1* | 12/2008 | Ruxton | ............... | H05B 37/029 |
| | | | | 315/193 |
| 2010/0260646 A1* | 10/2010 | Jorgensen | ............... | A61L 9/035 |
| | | | | 422/125 |
| 2010/0270943 A1* | 10/2010 | Cook | ............... | A61L 9/03 |
| | | | | 315/291 |
| 2011/0089252 A1 | 4/2011 | Rosener et al. | | |
| 2013/0170184 A1* | 7/2013 | Browder | ............... | A61L 9/015 |
| | | | | 362/96 |
| 2014/0375220 A1* | 12/2014 | Chen | ............... | G08B 15/00 |
| | | | | 315/154 |

OTHER PUBLICATIONS

Penelope Green, "What Good Taste Smells Like," The New York Times, http://www.nytimes.com/2014/06/19/garden/what-good-taste-smells-like.html?_r=0, Jun. 18, 2014, 12 pages.

\* cited by examiner

100

400

410

For 60Hz AC line voltage

| Pot Setting | Trigger angle/pulse width | Turn On Delay |
|---|---|---|
| 5V | <10° | min |
| 3.75V | 30° | 2ms |
| 2.5V | 90° | 4ms |
| 1.25V | 120° | 6ms |
| GND | OFF | max |

SYNCHRONOUS CONTROL OF LAMP BRIGHTNESS AND SAMPLE DIFFUSION

FIELD

The present application generally relates to sample diffusion techniques and, more particularly, to sample diffusion techniques employed in conjunction with additional sensory stimulus control techniques.

BACKGROUND

An aerial diffusion device, commonly known as a diffuser, is a device that diffuses a sample into the surrounding air. In one example, the sample is oil such as, e.g., fragrance oil, and the oil is diffusively delivered into the surrounding air as a fine mist or spray. Examples of diffusers include ultrasonic diffusers that vaporize the sample via vibration, evaporative diffusers that vaporize a sample by directing air through a filter where the sample is resting, heat diffusers that utilize a heat source to diffuse the sample, and nebulizing diffusers. Nebulizing diffusers work by using a pressurized air stream generated by an air pump with a specially designed nozzle. Advantageously, the rate of evaporation of a nebulizing diffuser is highly accelerated and occurs almost instantly. The air pump and nozzle, along with the shape of the diffuser bulb that holds the sample, cause the sample to atomize into a fine spray or mist for delivery into the surrounding air.

Fragrance diffusers have become very popular for use in homes and offices in order to deliver an olfactory stimulus in the form of a desired scent into a particular room or area of the home or office. Attempts have been made to provide a secondary sensory stimulus in conjunction with the olfactory stimulus provided by the fragrance diffuser. However, prior art attempts at such multiple sensory stimuli have experienced difficulties in coordinating the multiple devices that respectively provide the multiple sensory stimuli.

SUMMARY

Embodiments of the invention provide sample diffusion techniques employed in conjunction with synchronized lamp brightness control techniques.

By way of example only, in one illustrative embodiment, a sample diffuser apparatus comprises a sample container, a motor, a light source, and a control system. The sample container is configured to receive a sample to be diffused. The motor is operative to assist in diffusing the sample at a selectable transformation rate. The light source comprises an alternating current (AC) lamp. The control system is operatively coupled to the motor and the light source, wherein the control system comprises: a switch assembly comprising a potentiometer, wherein the potentiometer provides a voltage responsive to user interaction; and control circuitry operatively coupled to the switch assembly, the control circuitry configured to enable synchronous control of the transformation rate of the sample in the sample container and an intensity of light emitted by the AC lamp based on the voltage provided by the potentiometer.

The control circuitry, in an illustrative embodiment, comprises: lamp driver circuitry operatively coupled to the AC lamp; motor driver circuitry operatively coupled to the motor; and a microcontroller operatively coupled to the lamp driver circuitry and the motor driver circuitry, the microcontroller programmed to generate a first signal output to the motor driver circuitry and a second signal output to the lamp driver circuitry, wherein the second signal relates to the first signal to simultaneously control the intensity of the light based on the transformation rate.

In a further illustrative embodiment, a method for controlling diffusion of a sample comprises the following steps. In response to user interaction, a signal is generated from a control element of a sample diffuser assembly. The sample diffuser assembly comprises a sample container, wherein the sample container is configured to receive a sample to be diffused; a motor operative to assist in diffusing the sample at a selectable transformation rate; a light source, wherein the light source comprises an AC lamp; and control circuitry operatively coupled to the motor and the light source. A set of signals is generated, via the control circuitry in response to the signal generated by the control element, wherein the set of signals simultaneously control the light intensity of the AC lamp based on the transformation rate produced by the motor to diffuse the sample in the sample container.

Advantageously, in one example, embodiments provide a fragrance diffusion system for controlling the rate at which a fragrance is diffused and the intensity of a light bulb, in a simultaneous and synchronous fashion, within an environment in which the diffuser system is deployed.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 6 illustrates turn on delays for potentiometer settings, according to an embodiment of the invention.

DETAILED DESCRIPTION

Embodiments of the invention will be described herein with reference to a diffuser assembly having synchronous control of the rate at which a fragrance is diffused into a room and the intensity of the light emitted by an associated lamp. The diffuser assembly enables a user to selectively adjust the diffusion intensity ranging between a low level and a high level. A low diffusion intensity corresponds to a mild or subtle scent being introduced into the surrounding area, while a high diffusion level corresponds to a stronger scent being introduced. In various illustrative embodiments, the range can include continuous or discrete intensity levels between the low and high levels. A lamp in the diffuser assembly provides a visual indication of the adjustment of the diffusion intensity. That is, the brighter the light emitted by the lamp, the higher the diffusion intensity. Thus, a user can associate the light intensity output by the diffuser assembly with the diffusion intensity. The diffuser assembly further comprises electrical circuitry that functions to synchronously control the brightness of the lamp with the diffusion intensity. In one illustrative embodiment, the lamp is an incandescent lightbulb and the diffuser is a nebulizing diffuser comprising a glass bulb with a glass stopper into which fragrance oil is deposited.

While illustrative embodiments are described herein with respect to a sample being fragrance oil, it is to be appreciated that the inventive teachings are more broadly applicable to other types of diffusable oils including, but not limited to, essential oils, aromatic oils, and perfume oils.

Figure 1:
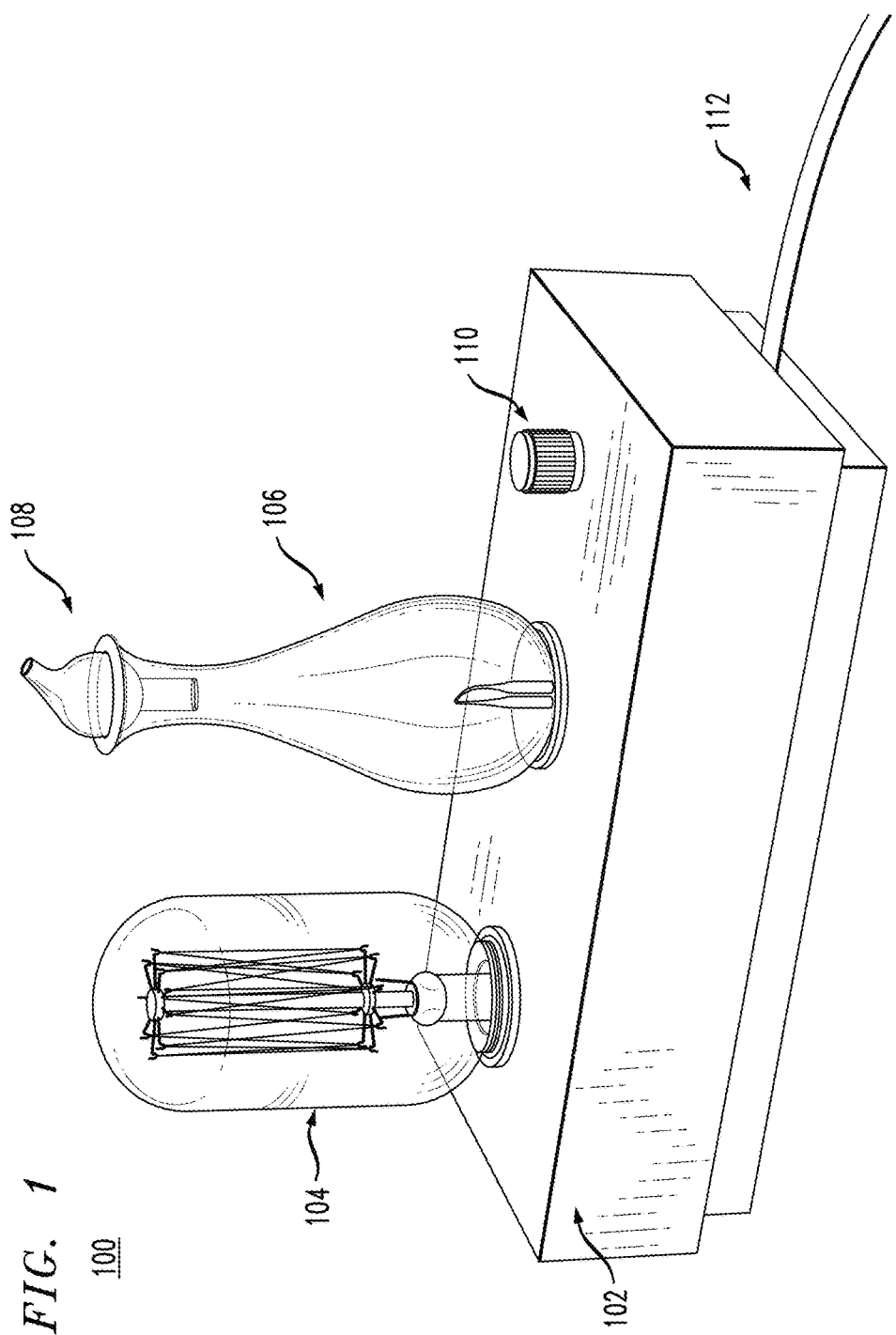
FIG. 1 illustrates a perspective view of a diffuser assembly, according to an embodiment of the invention.

FIG. 1 illustrates a view of a diffuser assembly 100 showing an example of the locations in which a control element (shown at least in part in FIG. 1 as user control 110), glass bulb 106, glass top 108, which is placed on top of the glass bulb, and lamp 104 may be located. In the exemplary illustration of FIG. 1, user control 110 is located on top of diffuser platform 102 and closer to a first side of diffuser platform 102. Glass bulb 106, into which fragrance oil (or other sample) is deposited, is located in proximity to the center of diffuser platform 102. The glass bulb may be more generally referred to as a sample container. Lamp 104, which may be a decorative type of bulb, is shown positioned closer to a second side of diffuser platform 102. However, such a placement is merely exemplary. Alternative placements of lamp 104, as well as the other components of diffuser assembly 100, are contemplated. It is to be appreciated that circuitry for controlling the diffuser and light components on top of the platform 102 are contained inside diffuser platform 102.

In one embodiment, lamp 104 is directly connected to an alternating current (AC) source. For example, lamp 104 may be an incandescent bulb, such as a decorative Edison-type incandescent bulb. In one embodiment, lamp 104 is rated at 40 Watts (W). However, the type of lamp and wattage rating should not be considered limiting.

As further shown in FIG. 1, electrical cord 112 (with a typical AC male plug that is not expressly shown) is supplied to connect AC power to diffuser assembly 100. The AC power supplied depends on the country in which diffuser assembly 100 will be used. Thus, alternative embodiments of diffuser assembly 100 are respectively configured to operate with the AC voltage level and frequency of the country in which they will be used. For example, AC power in the United States is typically provided between 110 AC Volts (VAC) and 120 VAC at 60 hertz (Hz), while France and other European countries typically operate between 220 VAC and 240 VAC at 50 Hz. Also contemplated with one or more alternative embodiments is a diffuser assembly 100 that operates in dual (50 Hz/60 Hz) environments and/or environments using other standard voltage levels and frequencies. It is to be appreciated that diffuser assembly 100 can be specifically designed and/or customized to provide its synchronous control functionalities for diffusion intensity and lamp intensity for the AC line power environment with which the diffuser assembly needs to operate. In one illustrative embodiment, as will be described herein, the diffuser assembly is configured to operate in a voltage range from 90 VAC up to 260 VAC, inclusive, and operate on frequencies of 50 Hz or 60 Hz.

Figure 2:
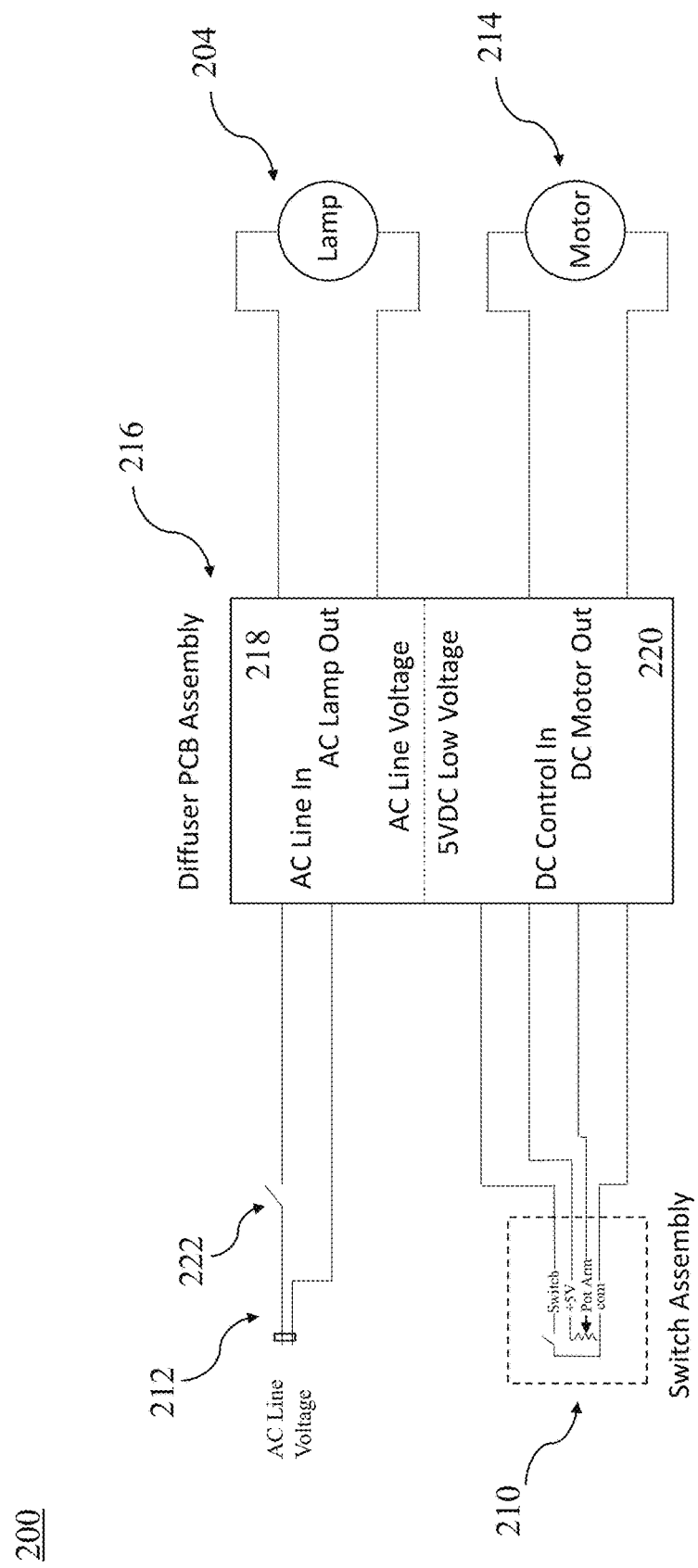
FIG. 2 is a top level block diagram of components of a diffuser assembly, according to an embodiment of the invention.

FIG. 2 illustrates a top level block diagram of components (collectively depicted as reference numeral 200) of a diffuser assembly, such as diffuser assembly 100 shown in FIG. 1, according to an illustrative embodiment. As shown, components 200 comprise switch assembly 210, AC line cord 212, diffuser printed circuit board (PCB) assembly 216, lamp 204, and motor 214. Components 200 may additionally comprise switch 222 operative to connect or disconnect the AC power. Switch 222 may be incorporated into switch assembly 210, or may be located separate from switch assembly 210. As discussed above, lamp 204 is directly connected to an AC source. In one embodiment, lamp 204 is an incandescent lamp. For example, lamp 204 may be an Edison-type decorative lamp having a rated wattage of 40 watts, although other types of incandescent lamps and other wattage ratings (more generally, any lamp that operates directly on AC power) are also contemplated. Motor 214 is coupled to the base of glass bulb 106 (FIG. 1) and is operative to control the diffusion rate, also referred to herein as transformation rate, of fragrance oil deposited within glass bulb 106. In one embodiment where the diffuser is a nebulizing diffuser, motor 214 is an air pump type motor. Switch assembly 210 provides both an on/off switch control and a potentiometer for synchronous and simultaneous control of motor 214 and the intensity of lamp 204, as will be explained in further detail below.

PCB assembly 216 includes analog circuitry 218 and digital control circuitry 220. Analog circuitry 218 operates to supply AC power to lamp 204, and convert the AC line power to a regulated direct current (DC) low voltage supply for use in digital control circuitry 220.

The components shown in FIG. 2 may be considered a control system for lamp 204 and motor 214.

Figure 3:
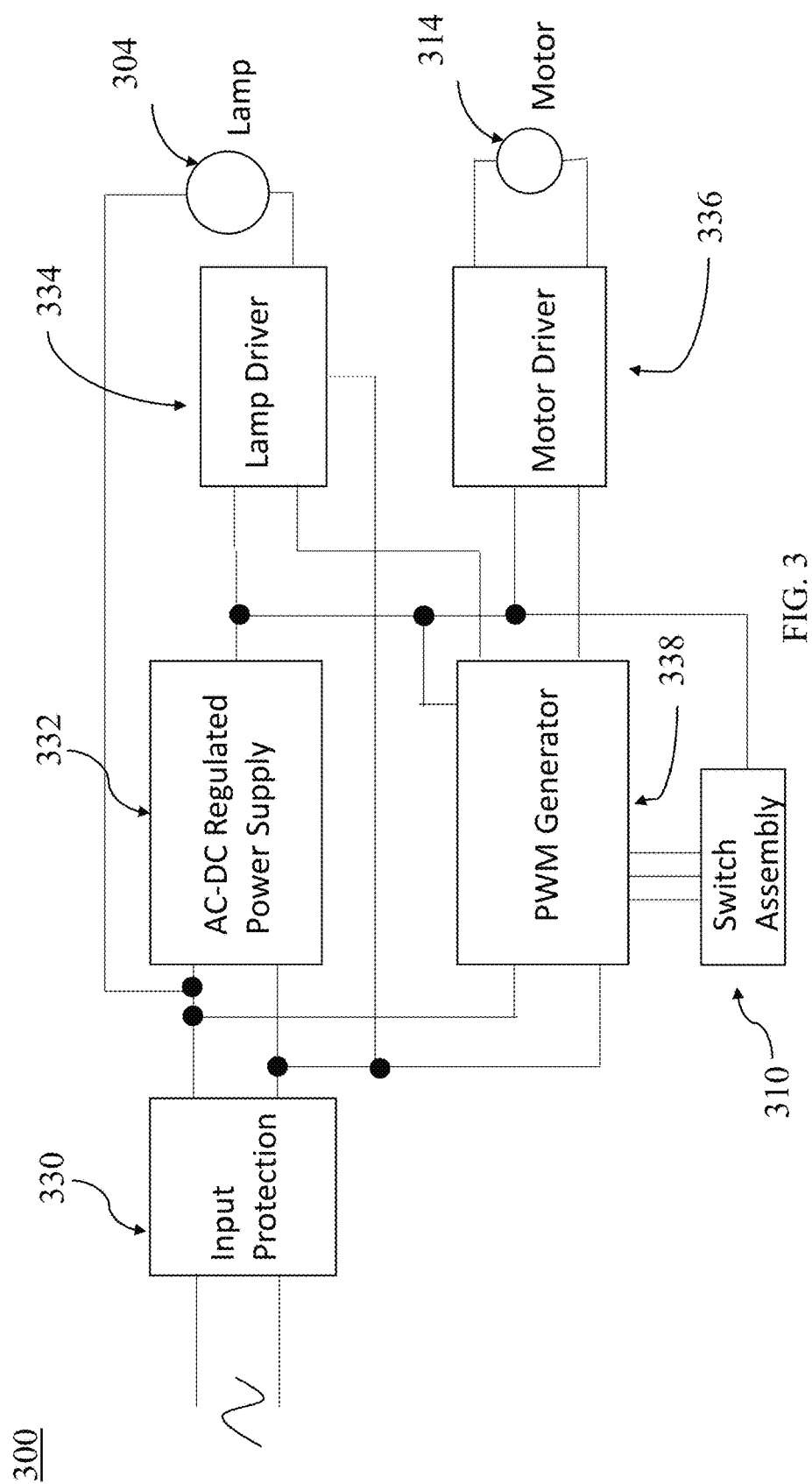
FIG. 3 is a more detailed level block diagram illustrating diffuser assembly control circuitry, according to an embodiment of the invention.

FIG. 3 illustrates a more detailed level block diagram (with the components collectively depicted by reference numeral 300). More particularly, various components shown in FIG. 3 may be considered components that are part of PCB assembly 216 (FIG. 2). Also, interface connections of PCB assembly 216 with lamp 304, motor 314, and switch assembly 310 are shown in FIG. 3. Thus, as shown, PCB assembly 216 comprises AC input protection circuitry 330, AC-DC regulated power supply circuitry 332, lamp driver circuitry 334, motor drive circuitry 336, and pulse width modulator (PWM) generator circuitry 338.

Input protection circuitry 330 interfaces the AC input line voltage with the remainder of the electronic components providing both short circuit protection as well as input transient voltage spike protection. The AC-DC regulated power supply 332 converts the input AC line voltage to a regulated DC low voltage supply for use by lamp driver circuitry 334, motor driver circuitry 336, PWM generator circuitry 338, and switch assembly 310. PWM generator circuitry 338 provides control signals to lamp driver circuitry 334 and motor driver circuitry 336, which control the intensity or brightness of lamp 304 and the speed of motor 314, respectively. The signal output to lamp driver circuitry 334 is related to the signal output to motor driver circuitry 336, such that a synchronous relationship is established between the transformation rate of the fragrance oil and the intensity of the light emitted by lamp 304. In one embodiment, the intensity of the light emitted by lamp 304 is proportional to the transformation rate of the fragrance oil.

In one embodiment, the transformation rate of the fragrance oil is also proportional to the speed of motor 314. As mentioned above, the intensity of light emitted from lamp 304 and the transformation rate of the fragrance oil, or speed of motor 314, are controlled by PWM generator circuitry 338. In one embodiment, PWM generator circuitry 338 provides controlled pulse width signals, each half cycle of the AC input, to lamp driver circuitry 334 and motor driver circuitry 336. Each of the pulse width signals are characterized by a start time delayed from the zero crossover of the AC input signal, and an end time at the following zero crossover of the AC input signal. The delay of the start time of the pulse may be controlled by the user via switch assembly 310. The width of the pulse width is directly related to the intensity of the light emitted from lamp 304 and the speed of motor 314. Specifically, a wider pulse width, resulting from a shorter start time delay, results in a higher light intensity and higher motor speed as compared to a narrower pulse width resulting from a longer start time delay.

It is to be appreciated that the pulse width of the signal output to motor 314 may be insufficient to cause motor 314 to start. Accordingly, in one embodiment, PWM generator circuitry 338 is pre-programmed to ensure that when the diffuser assembly is turned on, and switch assembly 310 is asserting a minimum pulse width, the pulse to motor driver 336 is of sufficient width to start the motor (which is readily determined during design of the control circuitry based on the operating specifications of the motor being used).

Recall that in FIG. 1, a control element, such as user control 110, is provided on diffuser assembly 100 for controlling both the intensity of the lamp and the diffusion rate of the fragrance oil. In one embodiment, the control element may be coupled to and/or part of switch assembly 310, such that manipulating the control element controls the operation of lamp 304 and motor 314. For instance, the control element is operative to turn both lamp 304 and motor 314 on and/or off. Additionally, manipulating the control element adjusts the start time delay of the pulse widths controlling lamp driver 334 and motor driver 336. Accordingly, manipulating the control element simultaneously and synchronously affects the intensity of light emitted from lamp 304 and the speed of motor 314.

Figure 4A:
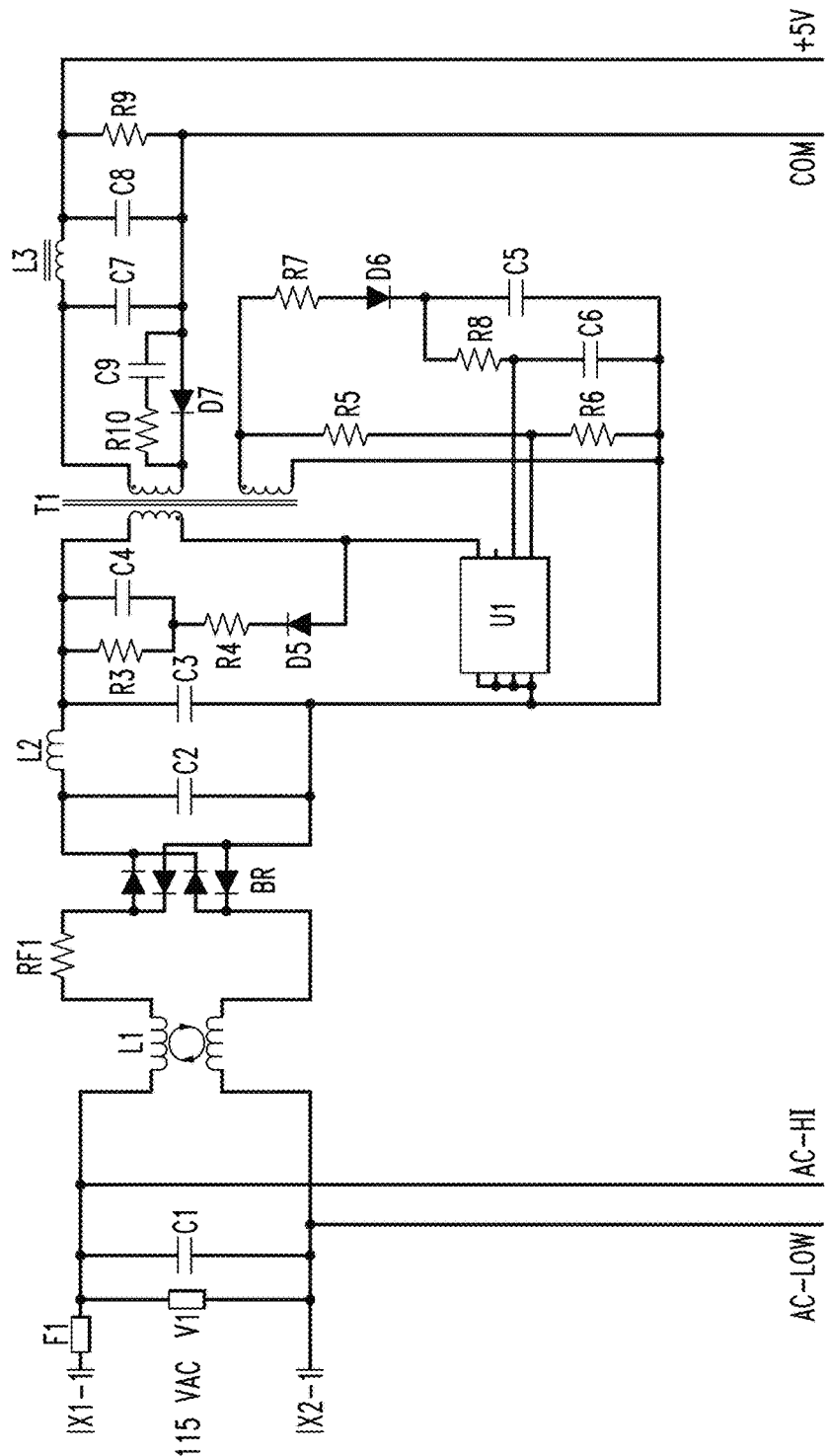
FIGS. 4A and 4B are schematic diagrams illustrating diffuser assembly control circuitry, according to an embodiment of the invention.
Figure 4B:
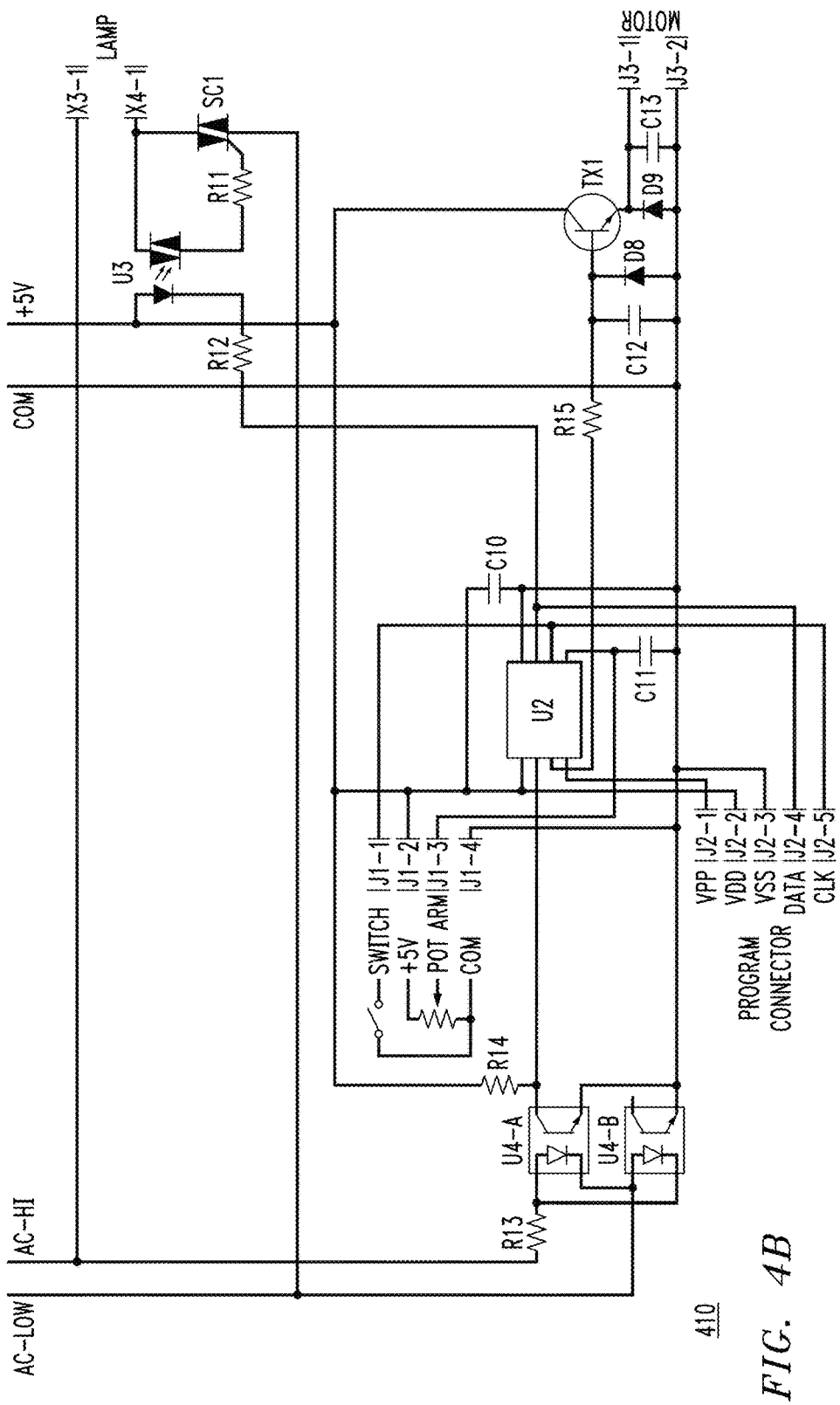

FIGS. 4A and 4B combined form the complete schematic diagram for the control circuit of an exemplary diffuser, e.g., diffuser assembly 100. With reference to FIG. 4A, the schematic illustrates a portion 400 of the control circuit related to AC input protection 330 and the AC-DC regulated power supply 332 of FIG. 3. The AC input voltage connected to terminals X1-1 and X2-1 may range from 90 VAC up to 260 VAC, inclusive, and may operate on frequencies of 50 Hz or 60 Hz. Components L1 through R9 referenced in FIG. 4A combine to form a power supply that tracks the line voltage to create a regulated 5 VDC voltage used by the circuitry shown in FIG. 4B. In addition, the AC voltage, AC-HI and AC-LOW, is used to supply power to the lamp and to provide a reference to determine the line voltage zero crossing point.

The input protection circuit (330) is shown having components F1, V1 and capacitor C1. F1 is a fuse providing protection against a significant system failure, such as a short circuit resulting in large currents drawn from the AC input. V1 is a metal oxide varistor, or MOV. The MOV operates to clamp the AC input during large differential line transients.

The remaining components form a single output, primary-side regulated flyback power supply. The power supply utilizes an integrated circuit U1, which is depicted in FIG. 4A as exemplary integrated circuit LNK625PG from Power Integrations™ However, other custom or commercially available power control circuitry that provide the same or similar functionalities as described herein may be employed. Integrated circuit U1 maintains constant voltage on the primary side of transformer T1, thereby eliminating the requirement for voltage control on the output side of the regulator. Full wave bridge rectifier BR rectifies the input AC signal after passing thru inductor L1 and resistor RF1, which is then filtered and provided to a first side of the primary winding of transformer T1. Inductor L2, capacitor C2 and capacitor C3 form a pi filter to reduce electromagnetic interference (EMI) noise. The second side of the primary winding of transformer T1 is driven by integrated circuit U1. Leakage inductance drain voltage spikes are limited by the clamp circuit provided by resistor R3, resistor R4, capacitor C4 and diode D5. In one embodiment, diode D5 is a surface mount ultra-fast rectifier. For example, diode D5 may be a 1 A, 1 KV diode.

Output regulation is controlled by a feedback circuit comprising a primary reference winding on transformer T1 and components R5-R8, diode D6 and capacitors C5-C6. Diode D6 may be a switching diode, such as a standard silicon 1N4148 diode. The secondary side of the transformer T1 is rectified by diode D7. Resistor R10 and capacitor C9 connected across diode D7 reduce high frequency ringing and EMI. The +5V output is filtered by components inductor L3, capacitor C7 and capacitor C8. Finally, resistor R9 provides a preload to maintain the output voltage if no load is applied. In one embodiment, diode D7 is a surface mount ultra-fast rectifier. For example, diode D7 may be a 1 A, 1 KV diode.

With reference to FIG. 4B, the schematic illustrates a portion 410 of the control circuitry related to control of the diffuser assembly. For example, FIG. 4B illustrates circuit details of switch assembly 310, PWM generator 338, lamp driver 334, and motor driver 336 of FIG. 3. In one embodiment, and as shown in FIG. 4B, switch assembly 310 (also referenced as 210 in FIG. 2) comprises a switch and a potentiometer. The switch assembly provides the user control of the diffuser, and is located separately from the PCB assembly (216 in FIG. 2) in this embodiment. The switch assembly is connected to circuitry on the PCB assembly via connector J1. In one embodiment, PWM generator 338 (depicted as U2 in FIG. 4B) includes a microprocessor operative to provide PWM signals to the lamp driver and the motor driver. For example, PWM generator U2 may be a PIC microcontroller. PIC stands for programmable (or peripheral) interface controller and refers to a family of microcontroller integrated circuits commercially available from Microchip Technology™ of Chandler, Ariz. However, various other types of microprocessors and/or microcontrollers may be utilized in accordance with the embodiments described herein.

The PWM generator U2 receives an input signal generated by a dual opto-isolator. For example, the dual opto-isolator may be an 8-pin SOIC dual-channel phototransistor output opto-isolator MOCD207 manufactured by Fairchild Semiconductor™. However, other custom or commercially available dual opto-isolators that provide the same or similar functionalities as described herein may be employed. In one embodiment, and as shown, the dual channel opto-isolator comprises opto-isolator U4-A and opto-isolator U4-B. The output of opto-isolator U4-A represents the zero crossover of the AC input signal and additionally provides isolation from the high voltage AC line to the low voltage DC circuitry. The input diode of opto-isolator U4-B is connected in reverse polarity and in parallel with the input diode of opto-isolator U4-A.

The switch and potentiometer arm of the switch assembly are connected to additional inputs of the PWM generator U2 through connector J1. PWM generator U2 utilizes the zero crossover signal generated by opto-isolator U4-A as a start point to which a delay is added before generating a pulse to be used to drive the lamp or motor. In one embodiment, the delay is a function of the voltage provided by the potentiometer located in the switch assembly. PWM generator U2 provides two pulse width controlled output signals, one for each of the lamp driver circuitry and the motor driver circuitry, respectively.

The operation of the PWM generator is as follows. If the switch contact in the switch assembly (210/310) is shorted to the circuit common, then the PWM generator U2 does not send a signal to either the lamp driver circuitry or the motor driver circuitry, and the pump motor and the lamp are completely off. When the control switch is rotated, the switch opens and the outputs are enabled. A linear voltage is generated by the potentiometer as it rotates clockwise. The potentiometer arm provides a voltage to the PWM generator U2, which drives the motor and lamp until full rotation is reached. Specifically, PWM generator U2 reads the voltage from the potentiometer, and calculates the PWM signal to send to the motor driver circuitry. The motor control signal is an increasing duty cycle PWM signal. This signal ramps up from the minimum level required to start the pump motor to the full 100%. Resistor R15, capacitor C12 and diode D8 operate to filter the PWM signal to the motor driver circuitry to smooth the signal to a DC level, which is then amplified through transistor TX1 in order to drive the pump motor. Transistor TX1 may be a bipolar power transistor, such as NJT4031 from ON Semiconductor™. Diode D9 and capacitor C13 are used to eliminate electrical noise generated by the motor as it runs. Diode D9 may be a switching diode, such as a standard silicon 1N4148 diode.

The PWM generator U2 also reads the zero crossing signal and calculates the delay time from the zero crossing to fire the TRIAC SC1 and power the lamp. TRIAC SC1 may be, for example, TRIAC BT131 from NXP™. However, other custom or commercially available TRIACs that provide the same or similar functionalities as described herein may be employed. As the potentiometer voltage ramps up, the PWM generator U2 calculates the proper firing angle to ramp the root mean square (RMS) power to the lamp so it brightens in a linear fashion as the arm of the potentiometer is rotated. In one embodiment, PWM generator U2 may be programmed to accommodate for the pulse width variations due to the difference in line frequencies of 50 Hz and 60 Hz. Programming of the microcontroller (microprocessor) is accomplished by connecting to the microcontroller via connector J2.

The lamp driver circuitry includes DIAC U3, TRIAC SC1, and current limiting resistors R11 and R12. In one embodiment, DIAC U3 is an opto-isolated DIAC, such as MOC3023 manufactured by Fairchild Semiconductor™. However, other custom or commercially available opto-isolated DIACs that provide the same or similar functionalities as described herein may be employed. The lamp is connected between AC power hot side, AC-HI, at bulb socket X3, while the neutral side of the bulb is switched through TRIAC SC1 via bulb socket X4. DIAC U3 maintains high voltage separation of the lamp voltage from the control circuitry.

At the proper firing angle, as controlled by the potentiometer, PWM generator U2 provides a low signal level to the input of DIAC U3 turning the output of the DIAC on, thereby connecting the neutral side of the lamp to the gate input of TRIAC SC1 through resistor R11. This, in turn, triggers TRIAC SC1 on, thereby turning on the lamp. PWM generator U2 then turns off DIAC U3 prior to the start of the next zero crossover detection. TRIAC SC1 then turns off as the AC voltage goes through its next zero crossover causing the lamp to go off. The above control signals continuously repeat for each half cycle of the AC line voltage. The brightness of the lamp is a function of the RMS power through the lamp, as controlled by the user's adjustment of the potentiometer.

PWM generator U2 is programmed such that the brightness of the lamp is synchronized to the speed of the motor. A rotation of the potentiometer which increases the voltage at the potentiometer arm results in an increase to the speed of the motor as well as an increase in the brightness of the lamp. A rotation of the potentiometer which decreases the voltage at the potentiometer arm results in a decrease to the speed of the motor as well as a decrease in the brightness of the lamp. Accordingly, the intensity of the light emitted from the light source is synchronously controlled with, and proportional to, the transformation rate of the fragrance oil.

Figures 5A, 5B, 5C:
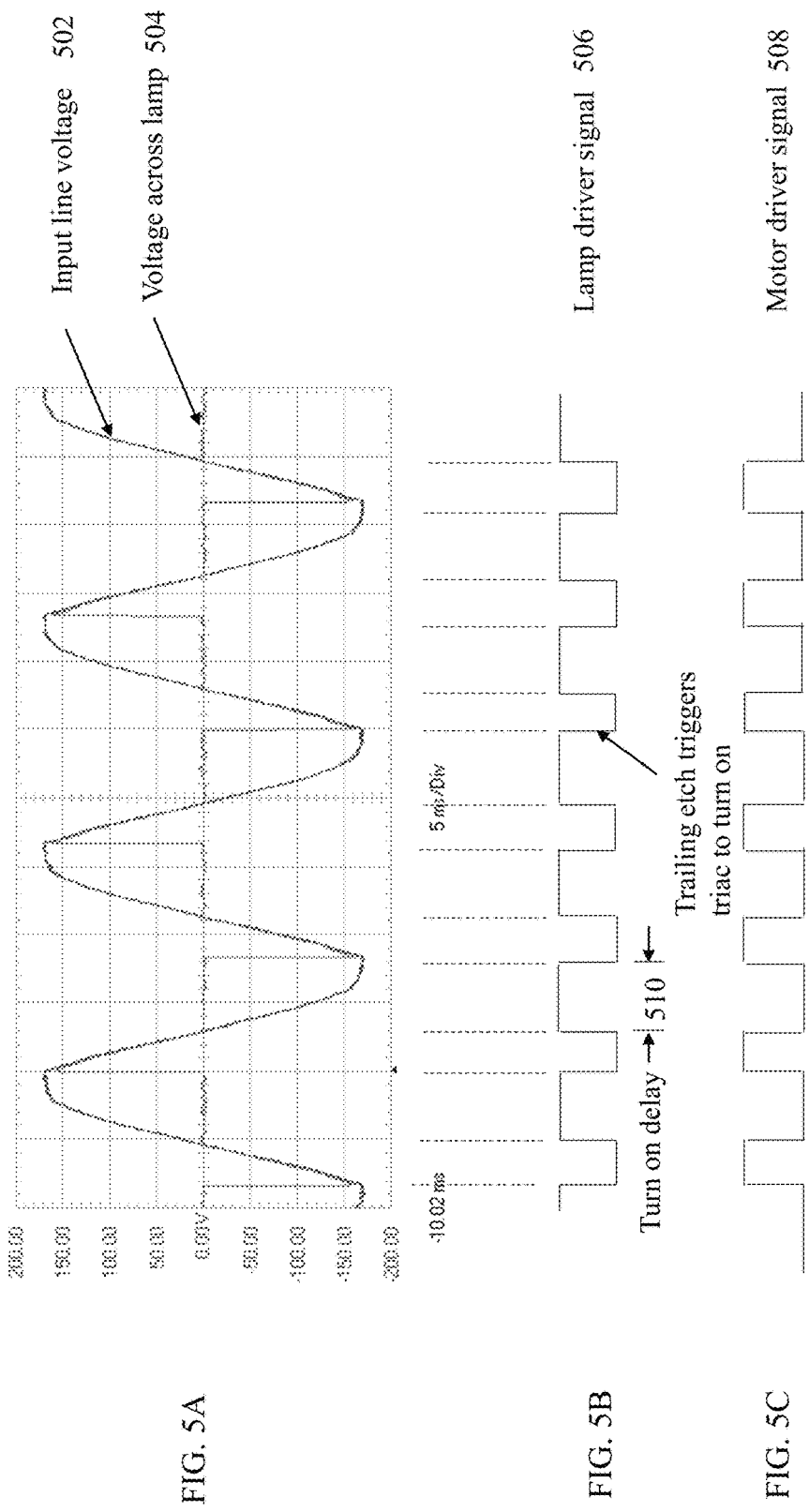
FIGS. 5A through 5C illustrate example signal waveforms associated with a diffuser assembly, according to an embodiment of the invention.

FIGS. 5A through 5C illustrate example signal waveforms associated with a diffuser assembly, according to an illustrative embodiment. More particularly, FIG. 5A illustrates an example of the waveform of a 120 VRMS, 60 Hz input line voltage 502. FIG. 5A further illustrates an example of the waveform 504 appearing across the lamp 304 resulting from the turn on delay generated by the PWM generator 338 to the lamp driver 334 as a function of the position of the potentiometer arm. That is, FIG. 5A shows the input AC line voltage waveform superimposed on the AC waveform appearing across a triac controlled lamp.

In the example waveforms illustrated, the potentiometer arm is positioned approximately midway between GND (ground) and 5V, resulting in a voltage of approximately 2.5 volts which is coupled to the input of the PWM generator 338. The PWM generator 338 converts this voltage into a PWM signal 506 (FIG. 5B) which drives the lamp driver 334 and PWM signal 508 (FIG. 5C) which drives the motor driver 336. For example, lamp driver signal 506 is a PWM signal which starts at a high level, i.e., 5V, at each zero crossing of the input line voltage 502. Lamp driver signal 506 remains high during a turn on delay period 510, during which the lamp remains turned off. The turn on delay period 510 is controlled by positioning the potentiometer arm. It is to be understood that positioning the potentiometer arm closer to 5V results in reducing the turn on delay 510, while positioning the potentiometer arm closer to GND results in an increase to the turn on delay 510.

In the example illustrated, the turn on delay 510 of lamp driver signal 506 is shown to be slightly more than a quarter cycle of the input line voltage 502 or approximately 5 milliseconds (ms). At the end of the turn on delay, lamp driver signal 506 from the PWM generator 338 transitions to a low level, i.e., GND, triggering TRIAC SC1 via opto-coupled DIAC U3. As illustrated by waveform 504, after the delay time 510, the AC line voltage is switched across the lamp 304 and the lamp turns on. When the AC voltage across the lamp crosses 0V (zero-crossing), the TRIAC turns off, turning the lamp off. After each zero crossing of the AC input line voltage 502, the PWM generator 338 generates a high level on lamp driver signal 506 for the duration of the turn on delay 510 and then transitions to GND for the remainder of the half cycle of the AC input line voltage 502. In another embodiment, signal 506 may not transition to GND for the remainder of the half cycle of the AC input line voltage 502, but rather may transition to GND for a period less than the remainder of the half cycle, such as, for example, 100 microseconds (usec). As the turn on delay 510 increases, the average power across the lamp decreases resulting in dimming the lamp. As the turn on delay 510 decreases, the average power across the lamp increases resulting in the lamp becoming brighter.

Similar to the operation of the lamp 304, the PWM generator 338 generates a PWM signal 508 to the motor driver 336. The motor drive PWM signal 508 from the PWM generator 338 is inverted from the lamp drive PWM signal 506. That is, signal 508 remains at a low level, GND, during the turn on delay period and then transitions to a high level, 5V, to drive the motor 314.

It should be noted that in other embodiments, the turn on delay for the motor driver 336 may be the same or different from the turn on delay for the lamp driver 334. The relative timing of the lamp driver turn on delay period and the motor driver turn on delay period is a function of synchronizing the lamp brightness with respect to the diffusion rate of the fragrance oil.

FIG. 6 illustrates an example of potentiometer settings and the resultant turn on delay and the angle in which the lamp 304 will turn on each half cycle of the AC input line voltage for the 60 Hz example. More specifically, table 600 shows illustrative turn on delays for potentiometer settings ranging between 5V and GND. The table is exemplary only and is therefore not intended to limit embodiments of the invention. Furthermore, the PWM generator 338 may be programmed to determine the turn on delays and/or other operational parameters by calculating values in real time or by storing and accessing pre-calculated values in a look up table. Also, in alternative embodiments, the motor 314 can run at frequencies other than 60/50 Hz (e.g., higher frequency F), but still yield the same or similar results. The inventive teachings are not limited to the AC line voltage characteristics described in illustrative embodiments. It is also to be appreciated that given the inventive teachings herein, those of ordinary skill in the art will realize straightforward alternatives to the exemplary implementation details described herein.

Furthermore, while not intended to be limiting, below is a table of component values of various components in embodiments shown in FIGS. 4A and 4B:

| Component | Value |
|---|---|
| RF1 | 10Ω |
| R3 | 270KΩ |
| R4 | 330Ω |
| R5 | 28.7KΩ |
| R6 | 4.42KΩ |
| R7 | 12Ω |
| R8 | 8.2KΩ |
| R9 | 820Ω |
| R10 | 18Ω |
| R11 | 470Ω |
| R12 | 470Ω |
| R13 | 33KΩ |
| R14 | 10KΩ |
| R15 | 100Ω |
| C1 | 0.1 uF |
| C2 | 6.8 uF |
| C3 | 6.8 uF |
| C4 | 1000 pF |
| C5 | 1 uF |
| C6 | 1 uf |
| C7 | 1000 uF |
| C8 | 470 uF |
| C9 | 1000 pF |
| C10 | 0.1 uF |
| C11 | 0.1 uF |
| C12 | 10 uF |
| C13 | 0.1 uF |
| L1 | 3 mH |

-continued

| Component | Value |
|---|---|
| L2 | 10 mH |
| L3 | 3.3 uH |
| F1 | 3.15 A |

Ω is ohms, uF is microfarads, uH is microhenrys, and mH is millihenrys. It is to be appreciated that the values given in the above table are examples, and thus other values can be used to achieve one or more of the advantages of the inventive teachings presented herein.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A sample diffuser apparatus, comprising:
    a sample container, wherein the sample container is configured to receive a sample to be diffused;
    a motor operative to assist in diffusing the sample at a selectable transformation rate;
    a light source, wherein the light source comprises an alternating current (AC) lamp; and
    a control system operatively coupled to the motor and the light source, wherein the control system comprises:
        a switch assembly comprising a single potentiometer, wherein the single potentiometer provides a linear voltage responsive to a rotational position of the single potentiometer controllable by user interaction;
        control circuitry operatively coupled to the switch assembly, the control circuitry configured to enable synchronous control of the transformation rate of the sample in the sample container and an intensity of light emitted by the AC lamp based on the linear voltage provided by the single potentiometer, wherein the control circuitry comprises:
            lamp driver circuitry operatively coupled to the AC lamp;
            motor driver circuitry operatively coupled to the motor; and
            a microcontroller operatively coupled to the lamp driver circuitry and the motor driver circuitry, the microcontroller programmed to generate a first signal output to the motor driver circuitry and a second signal output to the lamp driver circuitry;
        wherein each of the first signal and the second signal is characterized by a time delay corresponding to the linear voltage provided by the rotational position of the single potentiometer such that the time delay of each of the first signal and the second signal changes as the linear voltage changes based on the rotational position of the single potentiometer; and
        wherein the microcontroller, responsive to the rotational position of the single potentiometer, simultaneously controls the transformation rate of the sample being diffused based on the time delay of the first signal and the intensity of the light emitted by the AC lamp based on the time delay of the second signal such that the intensity of the light emitted by the AC lamp is proportional to the transformation rate of the sample being diffused.

2. The apparatus of claim 1, wherein the first and second signals are pulse width modulated signals, and wherein the width of each signal is based on the voltage provided by the potentiometer.

3. The apparatus of claim 2, wherein each of the pulse width modulated signals starts at the time delay after a zero crossover of an AC line input voltage.

4. The apparatus of claim 3, wherein a high side of the AC line input voltage is coupled to the light source at a first connection.

5. The apparatus of claim 4, wherein a second connection to the light source is an output of the lamp driver circuitry, and wherein the lamp driver circuitry comprises a TRIAC operatively coupled between the output of the lamp driver circuitry and a low side of the AC line input voltage to control operation of the light source.

6. The apparatus of claim 1, wherein the motor is operatively coupled between an output of the motor driver circuitry and a direct current (DC) voltage common line.

7. The apparatus of claim 6, wherein the motor driver circuitry comprises a transistor operatively coupled between the output of the motor driver circuitry and a DC supply, and wherein the transistor is operative to drive the motor responsive to the first signal.

8. The apparatus of claim 1, wherein the transformation rate is proportional to a speed of the motor.

9. The apparatus of claim 1, wherein the intensity of the light emitted from the light source provides a visual indication of the transformation rate.

10. The apparatus of claim 1, wherein the sample container comprises a glass bulb having a glass stopper, and wherein the sample is deposited in the glass bulb.

11. The apparatus of claim 1, wherein the sample comprises fragrance oil.

12. The apparatus of claim 1, wherein the motor comprises an air pump motor.

13. The apparatus of claim 1, wherein the AC lamp comprises an incandescent lamp.

14. A method for controlling diffusion of a sample, comprising:
providing, in response to a single potentiometer controllable by user interaction, a linear voltage based on a rotational position of the single potentiometer of a sample diffuser assembly, the sample diffuser assembly comprising a sample container, wherein the sample container is configured to receive a sample to be diffused; a motor operative to assist in diffusing the sample at a selectable transformation rate; a light source, wherein the light source comprises an AC lamp; and control circuitry operatively coupled to the motor and the light source; and
generating, via the control circuitry in response to the linear voltage provided by the single potentiometer, a set of signals;
wherein a first one of the set of signals and a second one of the set of signals are characterized by a time delay corresponding to the linear voltage provided by the rotational position of the single potentiometer such that the time delay of the first one and the second one of the set of signals change as the linear voltage changes based on the rotational position of the single potentiometer; and
wherein the control circuitry, responsive to the rotational position of the single potentiometer, simultaneously controls the transformation rate of the sample being diffused based on the time delay of the first one of the set of signals and the intensity of the light emitted by the AC lamp based on the time delay of the second one of the set of signals such that the intensity of the light emitted by the AC lamp is proportional to the transformation rate of the sample being diffused.

15. The method of claim 14, wherein the set of signals are pulse width modulated signals, and wherein the width of each signal is based on the linear voltage provided by the rotational position of the single potentiometer.

16. The method of claim 15, wherein each of the pulse width modulated signals starts at the time delay after a zero crossover of an AC line input voltage.

17. The method of claim 14, wherein the transformation rate is proportional to a speed of the motor.

18. A fragrance diffusion system, comprising:
a fragrance bulb, wherein the fragrance bulb is configured to receive fragrance oil to be diffused;
a motor operative to assist in diffusing the fragrance oil at a selectable transformation rate;
a light source, wherein the light source comprises an alternating current (AC) lamp;
a control system operatively coupled to the motor and the light source, wherein the control system comprises: a switch assembly for providing a linear voltage responsive to a rotational position of a single potentiometer controllable by user interaction; and control circuitry operatively coupled to the switch assembly, the control circuitry configured to enable synchronous control of the transformation rate of the fragrance oil in the fragrance bulb and an intensity of light emitted by the AC lamp based on the signal provided by the switch assembly, wherein the control circuitry comprises:
lamp driver circuitry operatively coupled to the AC lamp;
motor driver circuitry operatively coupled to the motor; and
a microcontroller operatively coupled to the lamp driver circuitry and the motor driver circuitry, the microcontroller programmed to generate a first signal output to the motor driver circuitry and a second signal output to the lamp driver circuitry; and
a platform configured to internally contain the motor and the control system, and externally support the fragrance bulb and the light source;
wherein each of the first signal and the second signal is characterized by a time delay corresponding to the linear voltage provided by the rotational position of the single potentiometer such that the time delay of each of the first signal and the second signal changes as the linear voltage changes based on the rotational position of the single potentiometer; and
wherein the microcontroller, responsive to the rotational position of the single potentiometer, simultaneously controls the transformation rate of the sample being diffused based on the time delay of the first signal and the intensity of the light emitted by the AC lamp based on the time delay of the second signal such that the intensity of the light emitted by the AC lamp is proportional to the transformation rate of the sample being diffused.

19. The system of claim 18, wherein the first and second signals are pulse width modulated signals, and wherein the width of each signal is based on the linear voltage provided by the rotational position of the single potentiometer.

20. The system of claim 19, wherein each of the pulse width modulated signals starts at the time delay after a zero crossover of an AC line input voltage.

* * * * *